(12) United States Patent
Biedermann et al.

(10) Patent No.: US 9,220,540 B2
(45) Date of Patent: Dec. 29, 2015

(54) BONE ANCHORING DEVICE AND BONE STABILIZATION DEVICE INCLUDING THE SAME

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 85 days.

(21) Appl. No.: 13/769,005

(22) Filed: Feb. 15, 2013

(65) Prior Publication Data

US 2013/0158605 A1    Jun. 20, 2013

Related U.S. Application Data

(63) Continuation of application No. 12/238,347, filed on Sep. 25, 2008, now Pat. No. 8,394,126.

(60) Provisional application No. 60/979,193, filed on Oct. 11, 2007.

(30) Foreign Application Priority Data

Oct. 11, 2007 (EP) ..................... 07019942

(51) Int. Cl.
*A61B 17/70* (2006.01)
*A61B 19/00* (2006.01)

(52) U.S. Cl.
CPC ......... *A61B 17/7032* (2013.01); *A61B 17/7037* (2013.01); *A61B 17/7004* (2013.01); *A61B 2019/304* (2013.01)

(58) Field of Classification Search
CPC ............... A61B 17/70; A61B 17/7004; A61B 17/70005; A61B 17/7007; A61B 17/7008; A61B 17/7032; A61B 17/7034
USPC .................................. 606/264–275, 301–320
See application file for complete search history.

(56) References Cited

U.S. PATENT DOCUMENTS 4,887,596 A * 12/1989 Sherman ........................ 606/305
4,946,458 A *  8/1990 Harms et al. .................. 606/305

(Continued)

FOREIGN PATENT DOCUMENTS

CA    2 577 436 A1    6/2006
EP    1 757 243 A1    2/2007

(Continued)

OTHER PUBLICATIONS

European Search Report for European Application No. 07019942.7, filed Oct. 11, 2007 in the name of Biedermann Motech GmbH, European Search Report dated Apr. 1, 2008 and mailed Apr. 9, 2008 (6 pages).

*Primary Examiner* — Jerry Cumberledge
(74) *Attorney, Agent, or Firm* — Christie, Parker & Hale, LLP

(57) ABSTRACT

A bone anchoring device, includes a receiving part for receiving a rod-shaped implant element, the receiving part having a first bore coaxial with a longitudinal axis and extending from a first end of the receiving part, and a recess extending from the first end to accomplish insertion of the rod-shaped implant element. The device further includes a bone screw having a threaded section for insertion into the bone and being fixed at or positionable at a second end of the receiving part and a fixation element provided to the first bore to fixate a rigid section of the rod-shaped implant element. The rigid section of the rod-shaped implant element has a first width, and the recess of the receiving part has a second width. The second width is larger than the first width, such that the recess may accommodate a stepped portion of the rod-shaped implant element that has an increased thickness.

14 Claims, 10 Drawing Sheets

(56) References Cited

U.S. PATENT DOCUMENTS

| | | | | |
|---|---|---|---|---|
| 5,120,171 | A * | 6/1992 | Lasner | 411/308 |
| 5,207,678 | A * | 5/1993 | Harms et al. | 606/267 |
| 5,437,669 | A * | 8/1995 | Yuan et al. | 606/278 |
| 5,474,551 | A * | 12/1995 | Finn et al. | 606/264 |
| 5,540,688 | A * | 7/1996 | Navas | 606/266 |
| 5,562,660 | A | 10/1996 | Grob | |
| 5,728,098 | A * | 3/1998 | Sherman et al. | 606/269 |
| 5,873,878 | A | 2/1999 | Harms et al. | |
| 5,957,953 | A | 9/1999 | DiPoto et al. | |
| 6,254,602 | B1 * | 7/2001 | Justis | 606/272 |
| 6,280,442 | B1 * | 8/2001 | Barker et al. | 606/60 |
| 6,565,566 | B1 * | 5/2003 | Wagner et al. | 606/267 |
| 6,875,212 | B2 | 4/2005 | Shaolian et al. | |
| 7,083,621 | B2 | 8/2006 | Shaolian et al. | |
| 8,029,544 | B2 | 10/2011 | Hestad et al. | |
| 8,083,777 | B2 | 12/2011 | Butters et al. | |
| 8,394,126 | B2 * | 3/2013 | Biedermann et al. | 606/261 |
| 2002/0133155 | A1 | 9/2002 | Ferree | |
| 2004/0122425 | A1 * | 6/2004 | Suzuki et al. | 606/61 |
| 2004/0249378 | A1 * | 12/2004 | Saint Martin et al. | 606/61 |
| 2005/0107788 | A1 | 5/2005 | Beaurain et al. | |
| 2005/0277922 | A1 | 12/2005 | Trieu et al. | |
| 2006/0025768 | A1 * | 2/2006 | Iott et al. | 606/61 |
| 2006/0095037 | A1 | 5/2006 | Jones et al. | |
| 2007/0161986 | A1 * | 7/2007 | Levy | 606/61 |
| 2007/0191842 | A1 | 8/2007 | Molz, IV et al. | |
| 2007/0213720 | A1 | 9/2007 | Gordon et al. | |
| 2007/0233085 | A1 | 10/2007 | Biedermann et al. | |
| 2007/0233091 | A1 | 10/2007 | Naifeh et al. | |
| 2008/0058812 | A1 | 3/2008 | Zehnder | |
| 2008/0161857 | A1 | 7/2008 | Hestad et al. | |
| 2008/0177331 | A1 | 7/2008 | Perez-Cruet et al. | |
| 2008/0183212 | A1 | 7/2008 | Veldman et al. | |
| 2008/0183214 | A1 * | 7/2008 | Copp et al. | 606/265 |
| 2008/0275456 | A1 * | 11/2008 | Vonwiller et al. | 606/99 |
| 2009/0093844 | A1 | 4/2009 | Jackson | |
| 2010/0137908 | A1 * | 6/2010 | Zhang | 606/246 |

FOREIGN PATENT DOCUMENTS

| | | |
|---|---|---|
| EP | 1 815 812 A1 | 8/2007 |
| GB | 2 312 624 A | 11/1997 |
| TW | 200726429 A | 7/2007 |
| WO | WO 01/97701 A1 | 12/2001 |
| WO | WO 2006/066685 A1 | 6/2006 |
| WO | WO 2006/119447 A1 | 11/2006 |

* cited by examiner

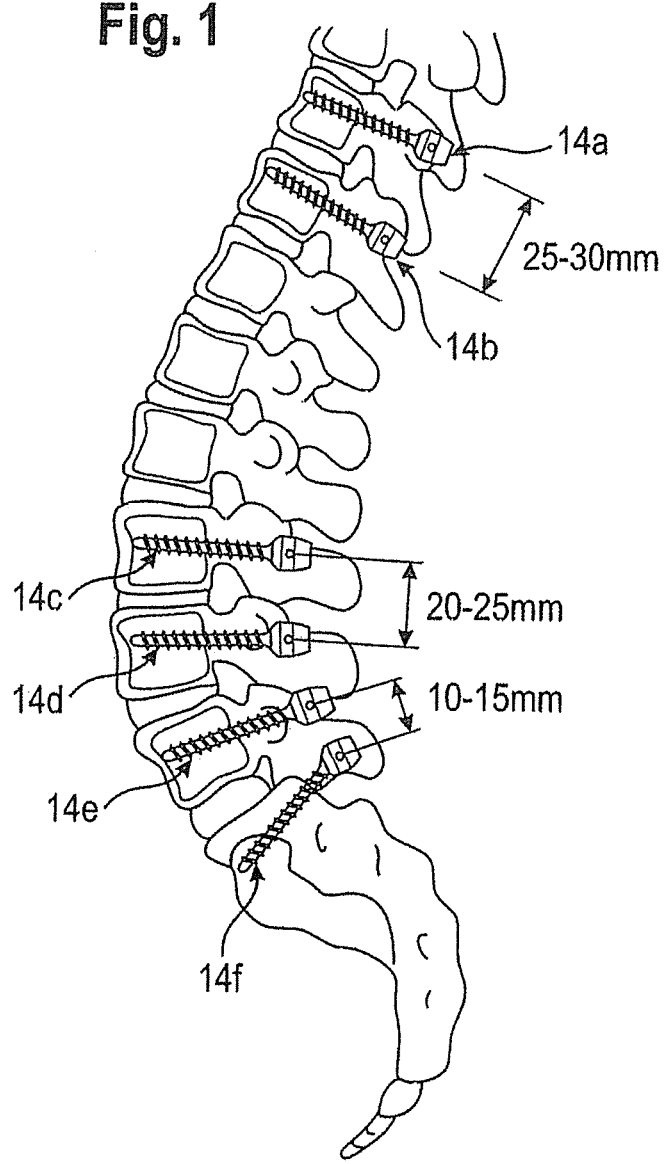

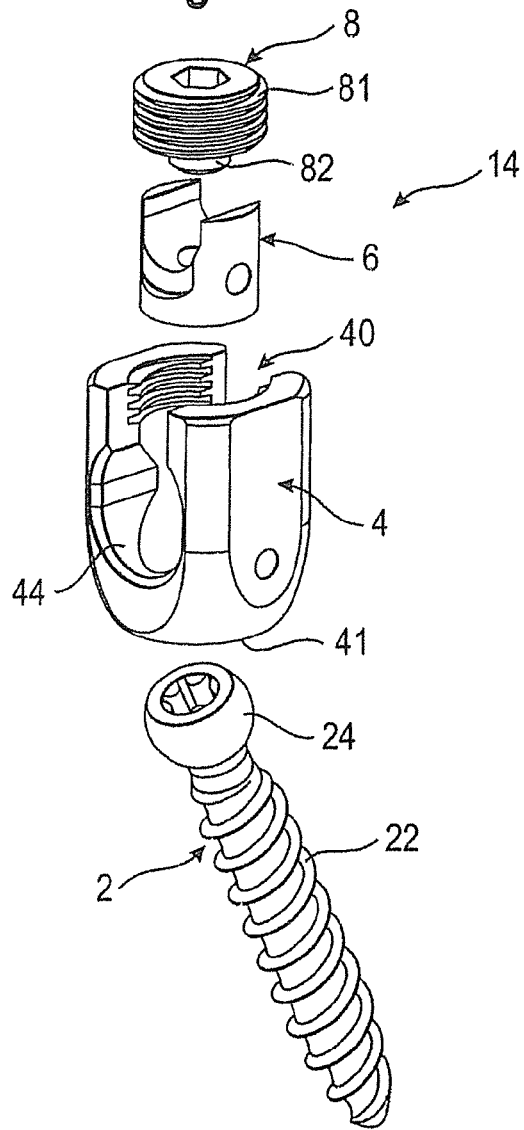
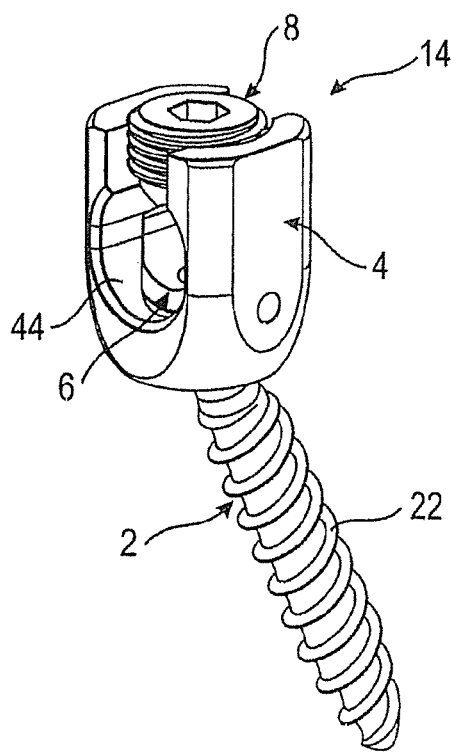

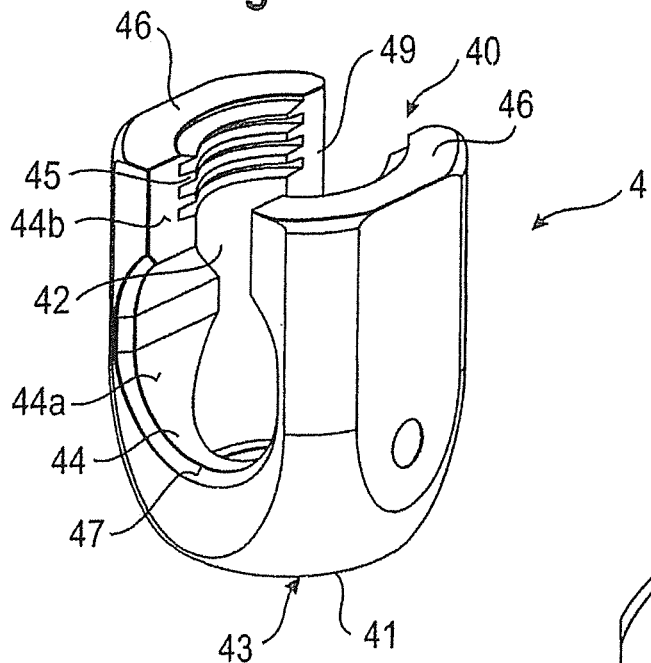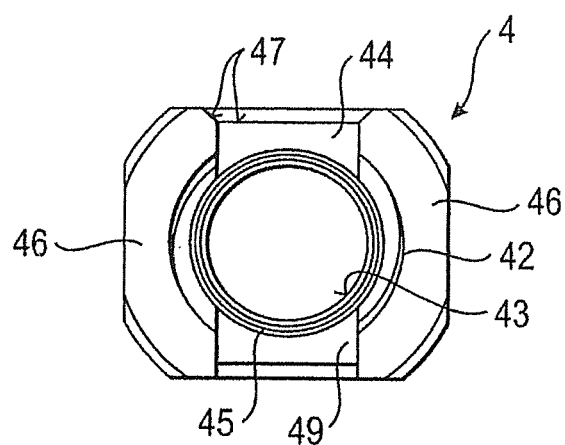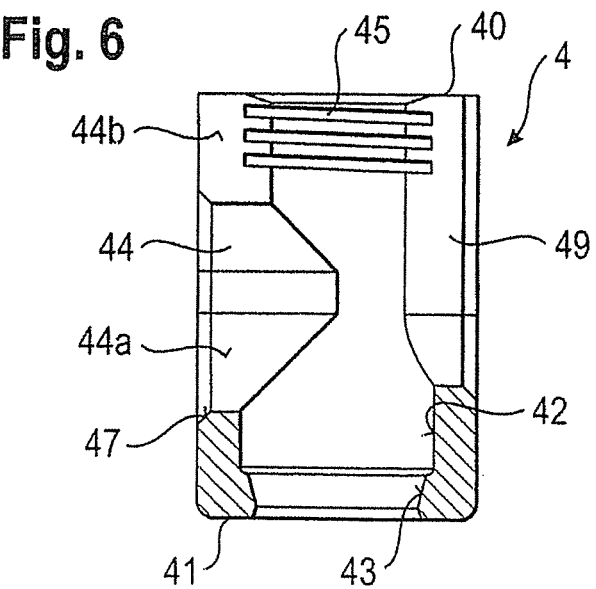

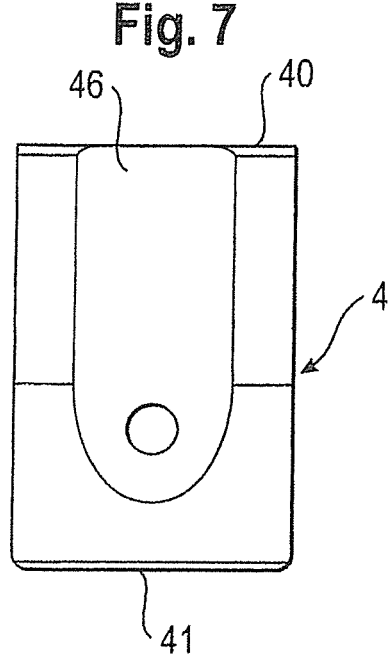
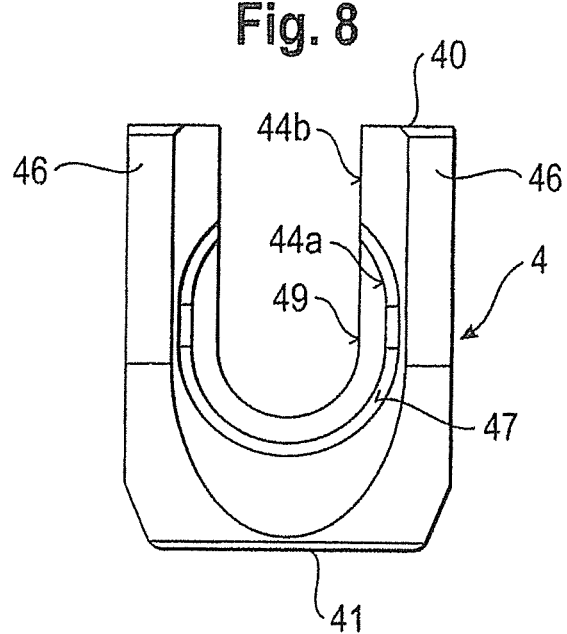
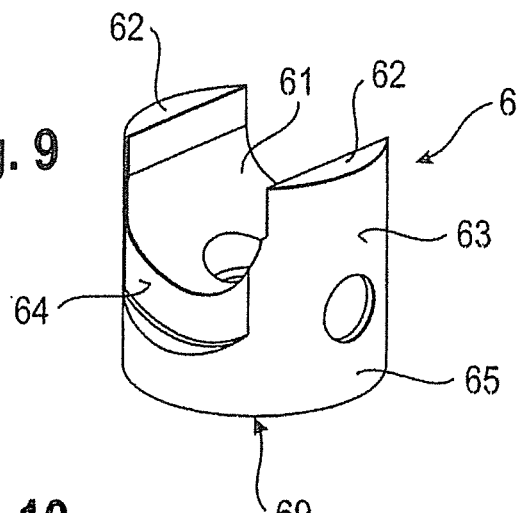
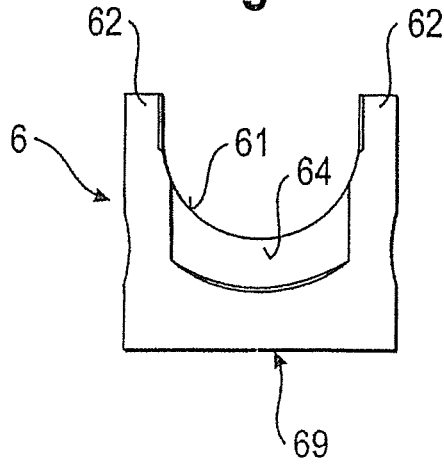
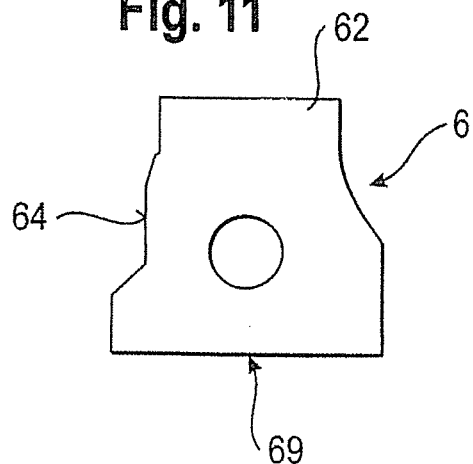

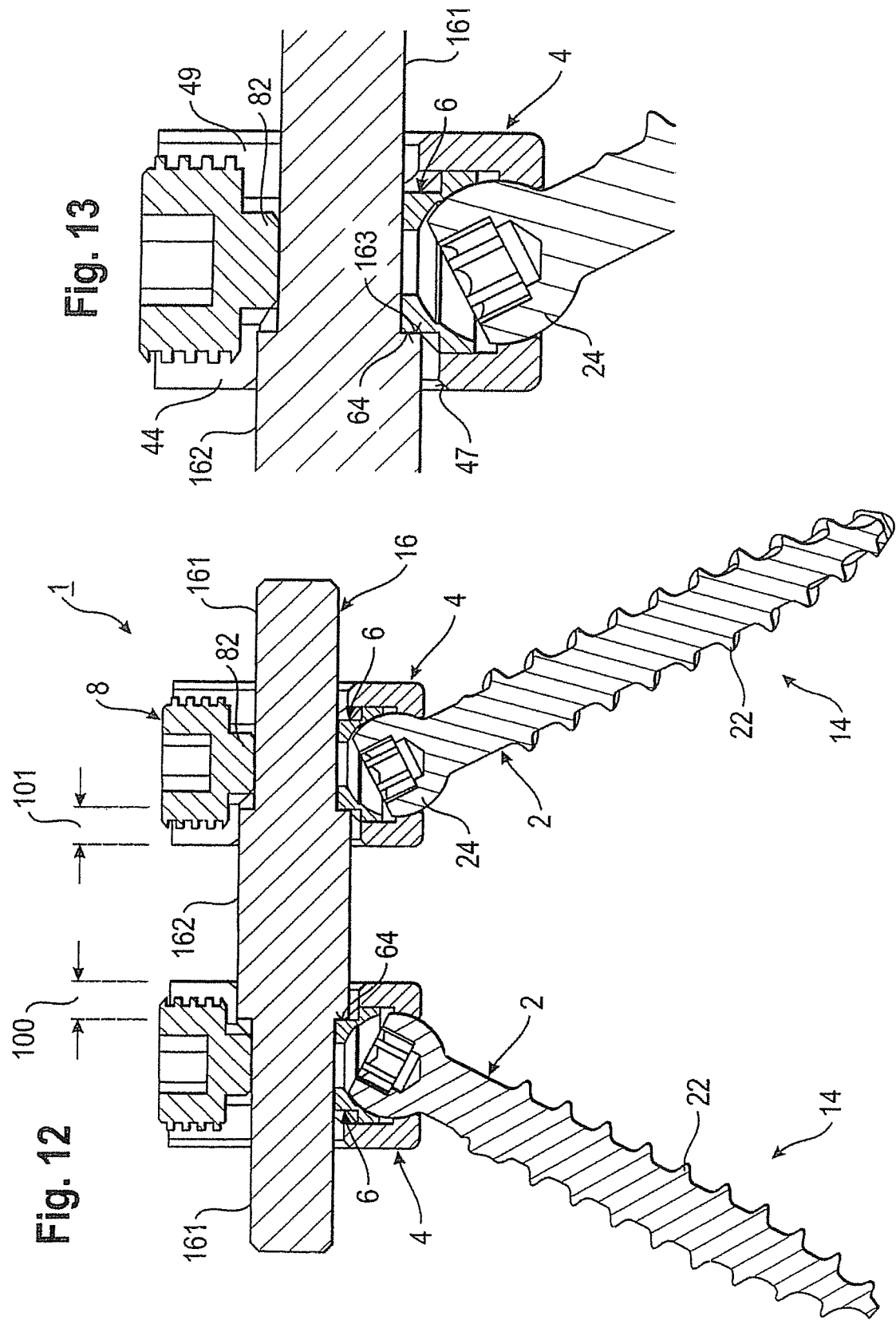

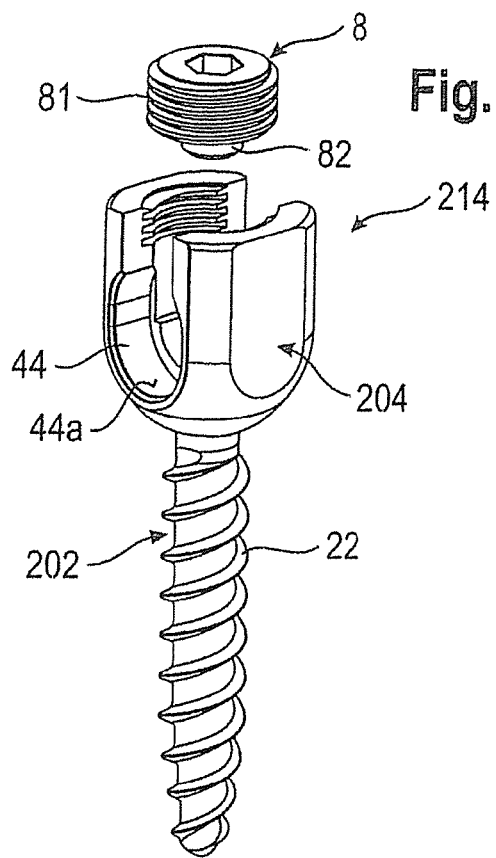
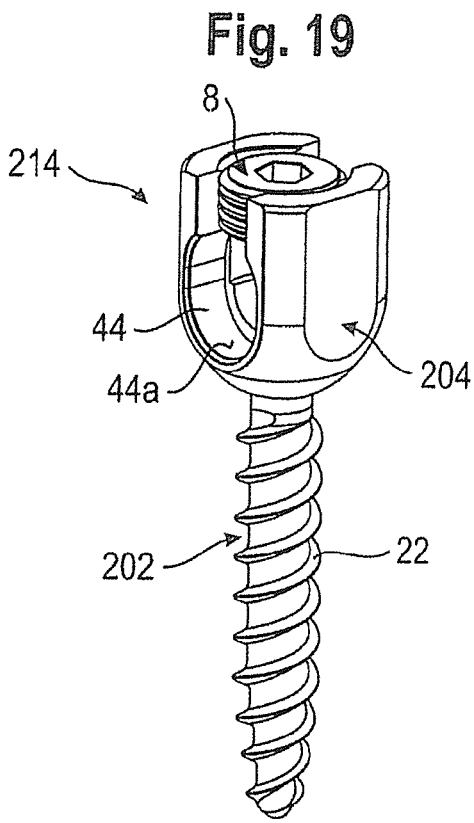
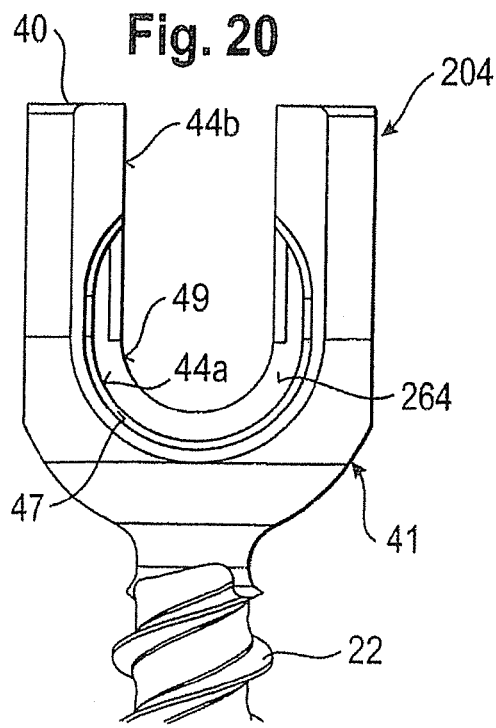
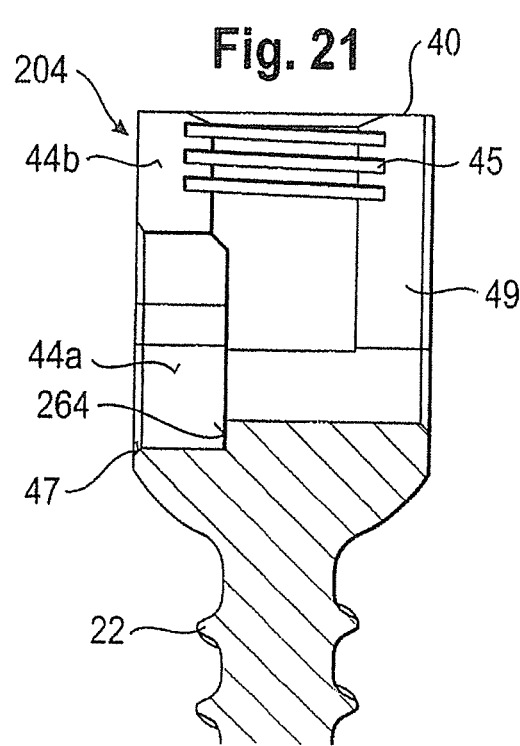

BONE ANCHORING DEVICE AND BONE STABILIZATION DEVICE INCLUDING THE SAME

CROSS-REFERENCE TO RELATED APPLICATION(S)

This application is a continuation of U.S. patent application Ser. No. 12/238,347, filed Sep. 25, 2008, now U.S. Pat. No. 8,394,126, issued on Mar. 12, 2013, which claims the benefit of U.S. Provisional Patent Application Ser. No. 60/979,193, filed Oct. 11, 2007, the contents of which are hereby incorporated by reference in its entirety, and claims priority from European Patent Application EP 07019942.7, filed Oct. 11, 2007, the entire disclosures of which are incorporated herein by reference.

BACKGROUND

The present application relates to a bone anchoring device and a bone stabilization device.

A bone anchoring device typically includes a receiving part for receiving a rod-shaped implant element, a bone screw having a thread section for insertion into a vertebral body of a spinal column, and a fixation element for fixating the rod-shaped implant element within the receiving part.

The rod-shaped implant element received by the above bone anchoring device may typically be connected to a further bone anchoring device that is similarly anchored in an adjacent vertebral bone in order to stabilize affected parts of the vertebral column.

One example of a bone stabilization device including two of the above bone anchoring devices and a rod-shaped implant element (in the following also referred to as a "rod element") is described in document EP 1757243 A1, by the same applicant. Therein, a rod element is disclosed which is composed of a rigid section, a flexible section, a bore formed within the rod element and a core. The core is provided inside the bore and extends through parts of the rigid sections and through the flexible section.

The flexible section may be made of a cylindrical pipe, into which a helical opening extending from the inner bore to the outer surface is formed. The resulting flexible section is characterized by its axial compression or expansion stiffness. The stiffness is achieved by a combination of pitch, web thickness and using biocompatible material's elasticity.

The core may freely slide inside the bore in axial direction at least with regard to one of its ends. Thereby, the free end is guided in a rigid section adjacent to the flexible section. The bending stiffness of the core is bigger than of the flexible section itself. Hence, the bending characteristics of the rod element are determined mainly by the core.

According to EP 1757243 A1, due to the presence of a bore which accommodates the core, the diameter or width of the rod element increases as compared with a common rod element, in which flexible components are not utilized.

The one specific bone anchoring device designed to receive the end section of the rod element is provided with small openings instead of the recesses. The end section of the rod element can be introduced through the openings, whose widths correspond to the reduced width of the end section.

Based on the above, there is a need for an improved bone anchoring device, which provides an enhanced flexibility with regard to a stabilization device including a rod element, and to provide a reliable bone anchoring device which facilitates the implantation of stabilization devices in cases where distance requirements with regard to two adjacently placed bone anchoring devices become very strong, i.e., cases where the mutual distances of those devices are considerably reduced.

SUMMARY

According to one aspect, there is provided a bone anchoring device having a receiving part for insertion of a rod-shaped implant element (in the following also referred to as a "rod element"). The recess extends from a first (upper) end of the receiving part towards a bottom section. At least in its bottom section, the recess attains a width (first width), which is larger than that of a section of the rod element (second width), which is to be fixated by the fixation element.

Hence, there is no play and the reliability of the anchoring device and the fixation of the rod element is increased by a quasi form-fit connection. This kind of connection may even improve the behaviour of the device with regard to strong forces exerted on the rod element in axial direction, which might else act to slip the rod through the receiving part.

When using such a stepped rod element in the recess, the minimum distance between the bone anchoring device is reduced. As will be described in the embodiments below, the stepped portion may represent a flexible section of the rod element. Thereby, in order to maintain desired properties like bending, compression, expansion, torsion stiffness, etc., in combination with fatigue strength, a minimum length of the flexible section is needed.

In case the mutual distance of two adjacent bone anchoring devices (more specifically: of two opposing surfaces of adjacent receiving parts) would decrease below that minimum length, a bone anchoring device as proposed herein may be utilized to increase the usable length for the flexible section by virtue of the recess being enlarged in width to receive portions of the flexible section.

According to another aspect related to a polyaxial anchoring device, a pressure element is provided which serves to transmit pressure exerted by the fixation element to a head section of the bone screw. The head section can be positioned in a bore at the bottom end of the receiving part. The pressure element has a cylindrical recess adapted to receive the rigid section of the rod element. The cylindrical recess has the first smaller width corresponding to the width of the rod element. The pressure element according to this aspect is further provided with a stop face. The stop face is designed to engage with an end face of the stepped portion of the rod element.

In an alternative aspect related to a monoaxial anchoring device, a cylindrical recess is provided at a bottom portion of a bore of the receiving part and is adapted to receive the rigid section of the rod element. Similar to the previous aspect, the cylindrical recess has the first smaller width corresponding to the width of the rod element. Further a stop face is oriented towards the recess having the larger width.

In one specific embodiment, the stop face is formed as a plane surface recessed from a generally cylindrically shaped surface of the pressure element.

According to this aspect, the pressure element may provide a form-fit connection with regard to the stepped rod element as well as with regard to a spherically or cylindrically shaped head section of the bone screw. Due to the recessed stop face, the stepped portion may reach into the inner space of the first bore formed in the receiving part, such that even more length can be reserved for accommodating the flexible section of the rod element, i.e., the mutual distance of the anchoring devices can be further reduced.

BRIEF DESCRIPTION OF THE DRAWINGS

The disclosure will be better understood with reference to specific embodiments of the disclosure when taken in conjunction with the accompanying drawings. Therein, FIG. 1 shows an illustration of the spinal column;

FIG. 2 shows an exploded view of a bone anchoring device according to an embodiment of the disclosure;

FIG. 3 shows the bone anchoring device of FIG. 2, but in an assembled state;

FIG. 4 shows in an enlarged perspective view a receiving part of the device according to FIG. 2;

FIG. 5 shows a top view of the receiving part of FIG. 4;

FIG. 6 shows a cross-sectional view of the receiving part according to FIG. 4;

FIG. 7 shows a side view of the receiving part according to FIG. 4;

FIG. 8 shows a front view of the receiving part according to FIG. 4;

FIG. 9 shows in an enlarged perspective view a pressure element of the device according to FIG. 2;

FIG. 10 shows a front view of the pressure element according to FIG. 9;

FIG. 11 shows a side view of the pressure element according to FIG. 9;

FIG. 12 shows a cross sectional profile of a bone stabilization device including the bone anchoring device of FIG. 2;

FIG. 13 shows an enlarged portion of FIG. 12;

FIG. 18 shows an exploded view of a bone anchoring device according to a second embodiment of the disclosure;

FIG. 19 shows a perspective view of the bone anchoring device of FIG. 18, with the fixation screw being screwed-in;

FIG. 20 shows in an enlarged front view a receiving part of the device according to FIG. 18;

FIG. 21 shows in a sectional view a receiving part of the device according to FIG. 18;

DETAILED DESCRIPTION

Figure 14:
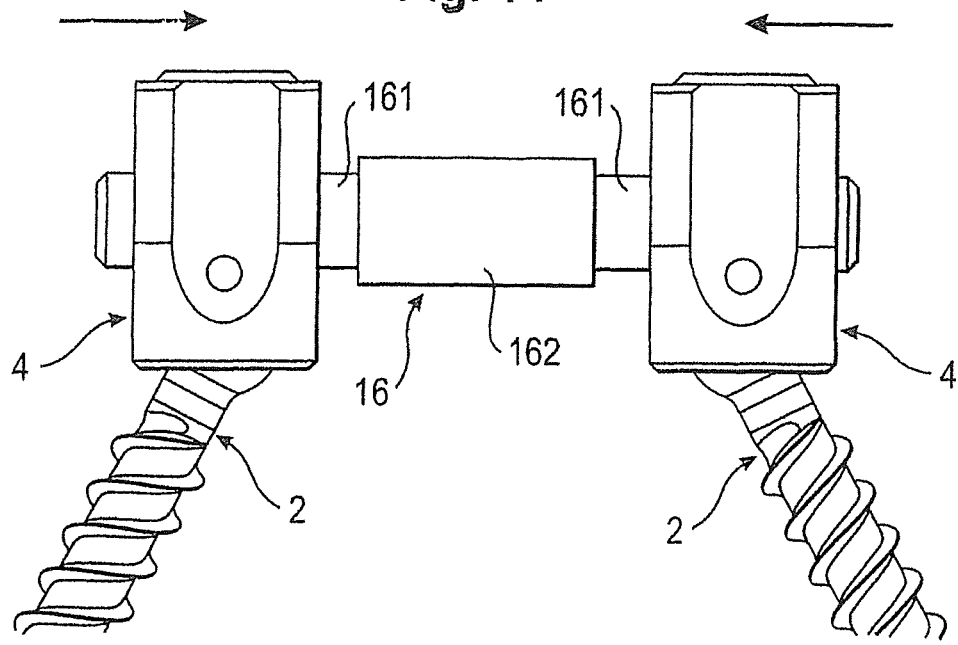
FIG. 14 shows a first step of assembling the bone stabilization device of FIG. 12 in a side view.

FIG. 1 shows a lower part of the spine anatomy in conjunction with variously positioned bone anchoring devices 14a-14f. The bone anchoring devices each include a bone screw and a receiving part for receiving and fixing, e.g., a head section of the bone screw. Each of the bone anchoring devices 14a-14f is anchored in one vertebrae of either the thoracic or lumbar spine.

As is apparent from FIG. 1, the interpedicular distance between two adjacent bone anchoring devices 14a and 14b in the high thoracic part decreases from 25 mm-30 mm towards values of 10-15 mm for respective bone anchoring devices 14e and 14f in the lower lumbar part (which stabilize L5-S1). As noted above, a rod element 16 designed to furnish the stabilization by connecting adjacent ones of the anchoring devices 14a-14f, and which is provided with flexibility and bending characteristics, must preserve a minimum length for a respective flexible section.

Hence, when considering the lower lumbar part, a flexible section requiring a length of, e.g., 15 mm cannot easily be positioned between respective receiving parts of conventional bone anchoring devices. It has to be noted that a typical receiving part may also contribute further 6-12 mm to the amount of needed distance.

FIGS. 2 and 3 show an embodiment of a bone anchoring device 14 as proposed herein. FIG. 2 shows an exploded view of the parts involved in a disassembled state, while FIG. 3 shows the device in an assembled state. First, the basic parts of the device which are partly known in the art will be described.

The bone anchoring device 14 includes a bone screw 2, a receiving part 4, a pressure element 6 and a fixation element 8. The bone screw 2 has a thread section 22 for insertion into the bone e.g., a vertebral body (not shown), and a head section 24. In this embodiment, the bone screw 2 has a spherically shaped head section 24, but the bone anchoring device shall not be limited to the specific shape and function of the head section 24 and/or the thread section 22. The materials selected for the components may be any biocompatible material or metals such as Titanium or Titanium alloy.

The receiving part 4 is of substantially symmetric form and has a first end 40 and a second end 41, which has a tapered profile. From the first end 40, there extends a first bore 42 to define an inner space of the receiving part 4, which also is of substantially cylindrical shape. At an upper portion of an inner wall of the bore 42, an inner thread 45 is formed which may engage with a corresponding outer thread 81 of the fixation element 8 (see also FIGS. 4-8).

The pressure element 6 is positioned within the first bore 42 between the fixation element 8 and the head section 24 of the bone screw 2. The bone screw 2 is accommodated within a second bore 43 adjacent to the first bore 42 and is positioned at the second end 41 opposite to the first end 40 of the receiving part 4. The pressure element 6 is provided with a bottom surface 69 (not shown in detail), which in this specific embodiment is arranged to yield a form-fit connection with the spherically shaped surface of the head section 24 of the bone screw 2 (see also FIGS. 9-11).

It may be noted herein that the specific type of connection of the bone screw 2 as described above refers to a polyaxial bone anchoring device. However, those of ordinary skill in the art will readily recognize that the function and effects of the bone anchoring device to be explained are similarly applicable to monoaxial bone anchoring devices described below with regard to a second embodiment.

Upon screwing-in the fixation element 8 into the thread 45 of the receiving part 4, pressure is exerted onto the rod element 16 inserted into receiving part 4. The pressure is then transmitted further to the pressure element 6 in order to lock the bone screw 2 with frictional force.

Next, the details of a modification as proposed herein will be described with particular reference to FIGS. 4-8, which show enlarged views of the receiving part 4.

The receiving part 4 is provided with two recesses 44 and 49, which extend from the first end 40. The recesses define two legs 46 of the receiving part 4 and are configured to receive the rod element 16 into the receiving part 4. The first recess 44 has substantially the shape of a reversed keyhole. The first recess 44 has a bottom section 44a and an upper section 44b, wherein the bottom section has a larger width (width as measured in a direction perpendicular to the axis of the inserted rod element and perpendicular to the longitudinal axis of the receiving part 4), and the upper section has a smaller width. For example, the width of the bottom section can be 7.5 mm and the width of the upper section can be 5.5 mm.

The bottom section 44a has a substantially circular or oval shape (see FIG. 8). It has an enlarged width in order to accommodate a stepped portion of the rod element 16. The second recess 49 on the back side in FIGS. 4 and 8, or on the right side in FIG. 6 is of the conventional type having a U-shape. Its width in its upper section as well as in its bottom section can be the same as the upper section 44b. For example, the width can be 5.5 mm.

An edge 47 defined by an intersection of the an inner wall of the bottom section 44a of the first recess 44 with an outer surface of the receiving part 4 is chamfered in order to facilitate insertion of a stepped portion of the rod element 16 upon assembly as will be explained below.

Next, details of the pressure element 6 modified as proposed herein are explained with reference to FIGS. 9-11. The pressure element 6 has two leg portions 62, separated by a cylindrical recess 61, and an annular base portion 65. The pressure element further has a substantially cylindrical outer surface 63. The cylindrical recess 61 is designed to receive the rigid section 161 of the rod element 16 and therefore has a corresponding width (e.g., 5 mm) in order to fit the same. The cylindrical recess has a longitudinal axis which upon insertion of the pressure element in the first bore 42 of the receiving part 4 is oriented perpendicular to the longitudinal axis of that bore 42.

The pressure element 6 further has a stop face 64, which is arranged as a plane surface recessed from the generally cylindrical outer surface 63. The stop face 64 is arranged to abut on the end face 163 of the stepped portion 162 of the rod element 16, or vice versa. The stop face 64 is accordingly shaped as an annular segment, which becomes apparent from the front view of FIG. 10. Preferably, the end face of the stepped portion is also represented by a plane surface perpendicular to the longitudinal axis of the rod, or of the cylindrical recess respectively.

It may be noted that the fixation element 8 in this embodiment has at its bottom end an extension 82. The extension 82 has a decreased diameter smaller than the threaded section. This decreased diameter allows the stepped portion 162 to be accommodated in the inner space of the first bore 42 of the receiving part 4. The length of the extension 82 along the longitudinal direction of the bore 42 is equal to or larger than the height of the step due to the stepped portion 162 of the rod element 16.

A bottom face of this extension 82 exerts pressure onto the rigid section 161 of the rod element 16, while an angular bottom face (not shown) of the threaded portion of the fixation element 8 may, for example, exert a pressure onto legs 62 of the pressure element 6.

FIG. 12 shows a cross-sectional view of a bone stabilization device 1 including two of the bone anchoring devices 14 as detailed above and a stepped rod element 16. FIG. 13 shows an enlarged detail of FIG. 12. The stepped portion 162 in this embodiment represents a flexible section of the rod element 16 comprising for example a helically opened pipe enclosing a bore in which a core being slidable at least at one end thereof is disposed with properties similar to the rod element in EP 1757243.

The stepped portion extends through respective first recesses 44 (due to the bottom section 44a) and into the internal spaces (due to the stop face 64) of the receiving parts 4 of the corresponding bone anchoring devices 14, for example devices 14e and 14f in FIG. 1. Portions 100, 101 of length as schematically indicated in FIG. 12 may thus be saved to accommodate the stepped portion between the receiving parts 4. For example, the lengths 100, 101 can be each 2-4 mm. The minimum length to accommodate the stepped portion is thus reduced to, for example, 9-11 mm, which may comply with the requirements applicable with regard to the L5-S1 stabilization (see FIG. 1).

Figure 15:
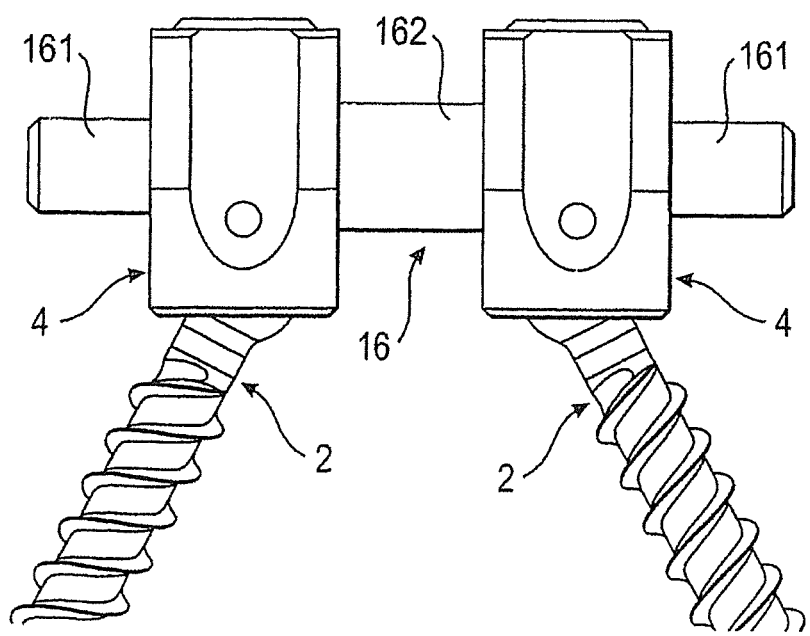
FIG. 15 shows a second (final) step of assembly of the bone stabilization device of FIG. 14.
Figure 16:
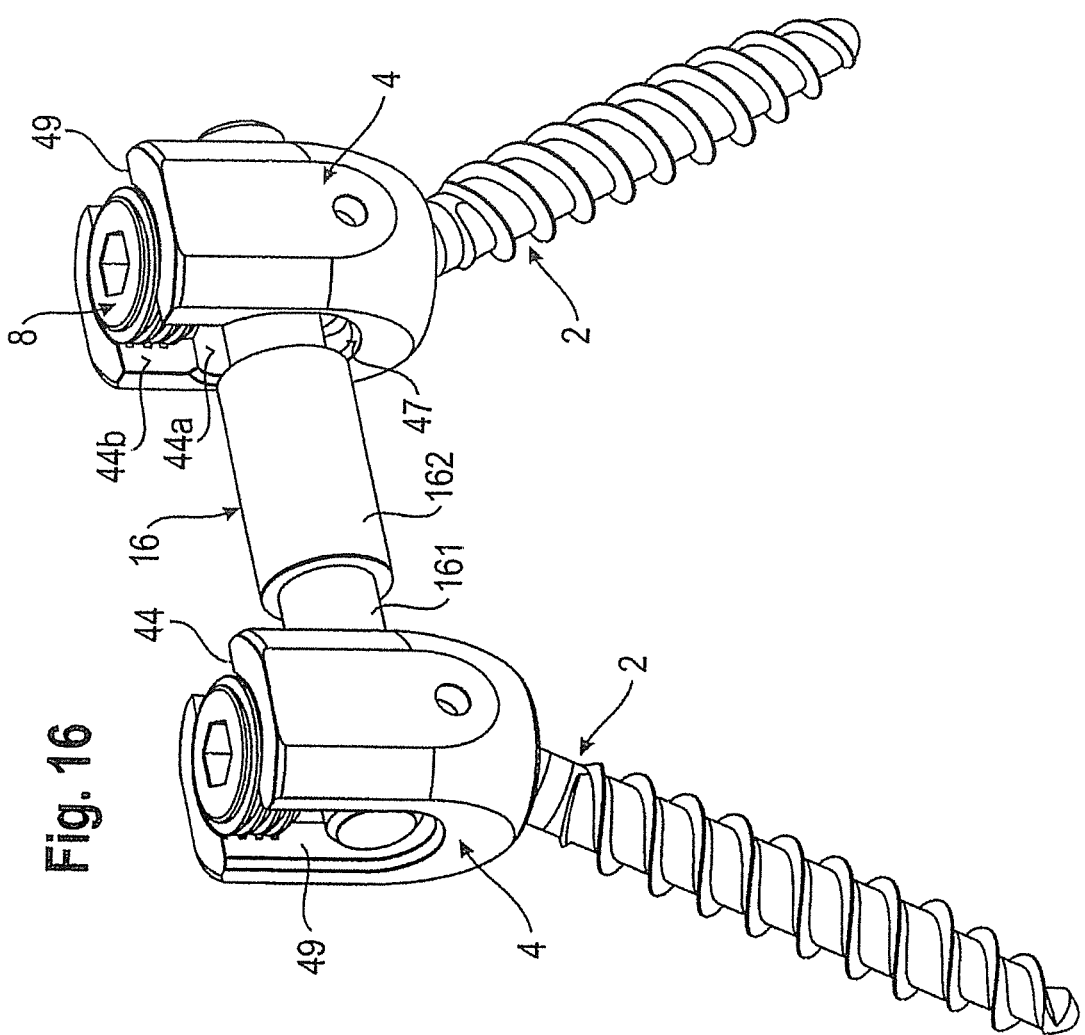
FIG. 16 shows a first step of assembling the bone stabilization device of FIG. 12 in a perspective view.
Figure 17:
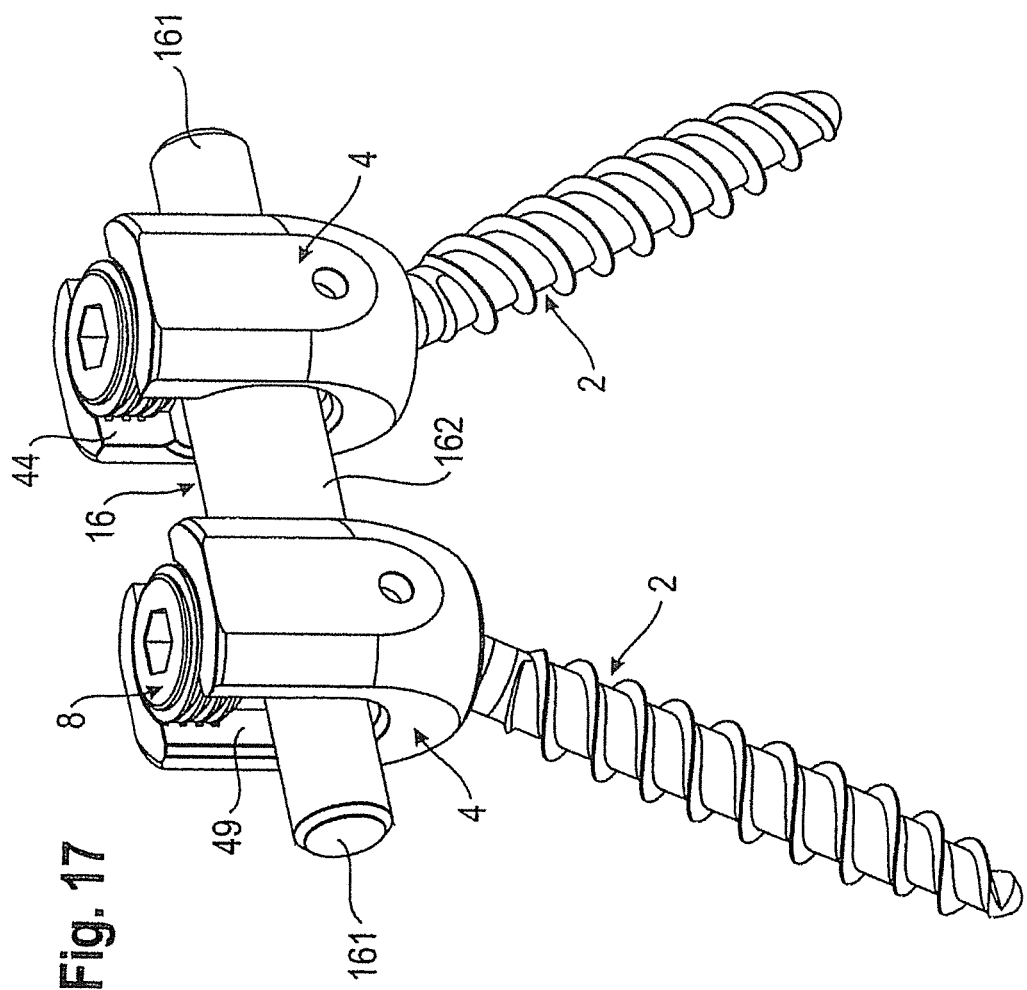
FIG. 17 shows a second (final) step of assembly of the bone stabilization device of FIG. 14 in a perspective view.
Figure 22:
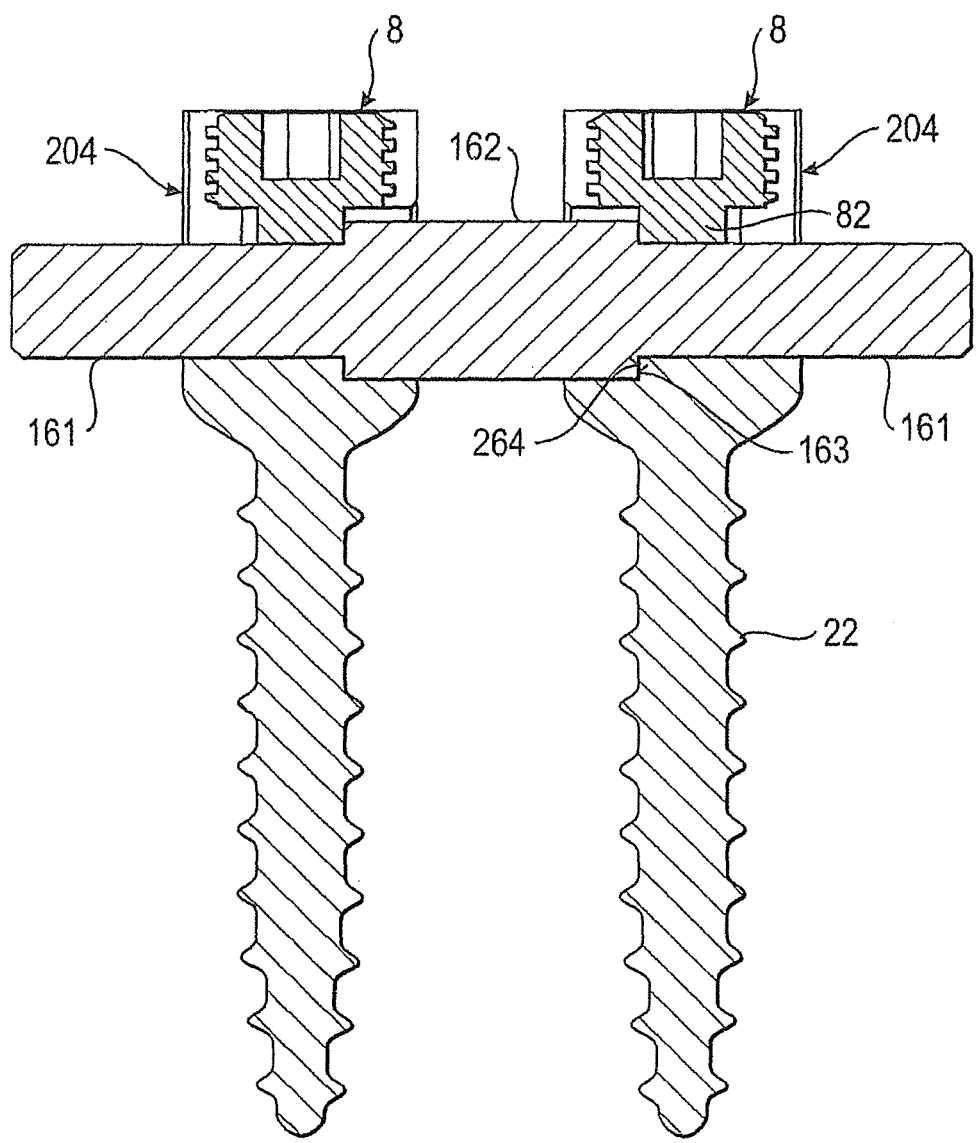
FIG. 22 shows a sectional view of the bone stabilization device according to the second embodiment.

FIGS. 14-17 illustrate the assembly process of the bone stabilization device 1. FIGS. 14, 15 show side views, while FIGS. 16 and 17 show perspective views of respective steps. First, the bone screws 2 are inserted into the receiving parts 4 through the first and second bores 42, 43 followed by anchoring the screws 2 in the respective bones. Then, the rigid sections 161 of the stepped rod element 16 are inserted into recesses 44, 49. The fixation elements 8 are then screwed in but are not yet fastened (FIGS. 14, 16).

Next, the two receiving parts 4 are shifted towards each other to shorten the mutual distance (indicated by arrows in FIG. 14). The stepped portion 162 thereby enters into each of the bottom sections 44a of the recesses 44 wherein the chamfered edges 47 of the recesses 4 help compensate for slight misalignments.

Finally, the end faces 163 of the stepped portions 162 abut on the stop faces 64 of the pressure elements 6 (FIGS. 15, 17).

Another embodiment is illustrated with respect to FIGS. 18-22. This embodiment relates to a monoaxial bone anchoring device 214. As compared with the first embodiment, similar components are denoted with the same reference numerals. In the following section only different features of the second embodiment are described.

In this embodiment, the bone screw part 202 is integrally formed with the receiving part 204. Thus the thread section 22 extends from the bottom end 41 of the receiving part in a fixed direction (i.e., not rotatable prior to fixation). Hence, contrary to the first embodiment, there is neither a pressure element nor second bore present in this anchoring device. Instead, the first bore 42 of the receiving part has a bottom end, at which is formed a cylindrical recess 261, which is similarly adapted to receive the rigid section 161 of the rod element 16.

Similar to the first embodiment, a plane stop face 264 is oriented towards a section 44a of the reverse key-shaped recess 44, which has the larger width to receive the stepped portion 162 of the rod element 16. The plane of the stop face 264 extends perpendicular to the longitudinal axis of the cylindrical recess 261, and also similar to stop face 164 according the first embodiment, intersects the inner space of the first bore.

It will become apparent to the person skilled in the art, that the modifications proposed herein may be embodied with various other configurations while yielding similar effects without departing from the scope as set forth in the appended claims.

What is claimed is:
1. A bone anchoring device, comprising:
   a receiving part for receiving a rod-shaped implant, the receiving part having a first end, a second end, a sidewall extending between the first end and the second end, a first bore extending coaxially with a longitudinal axis of the receiving part from the first end, and first and second recesses each extending into the sidewall from the first end, the first and second recesses being positioned and configured for insertion of a rod-shaped implant through the receiving part;
   a bone screw having a threaded section for insertion into a bone; and
   a fixation element configured to fix a rod-shaped implant in the first and second recesses;

wherein when the receiving part and the fixation element are assembled together, the first recess of the receiving part has a shape of an inverted keyhole, with a bottom section having a second width and an upper section oriented towards the first end of the receiving part having a first width smaller than the second width, and wherein a greatest width of the second recess of the receiving part is less than the second width.

2. The bone anchoring device of claim 1, further comprising the rod-shaped implant comprising a rigid first section having substantially the first width, and a stepped portion having a greater thickness than the first width, such that the first recess of the receiving part is configured to accommodate the stepped portion of the rod-shaped implant.

3. The bone anchoring device of claim 1, wherein the bone screw is fixedly attached to the receiving part.

4. The bone anchoring device of claim 1, wherein the bone screw is pivotably connected to the receiving part.

5. The bone anchoring device of claim 4, further comprising a pressure element configured to be inserted in the receiving part and to be arranged between a head of the bone screw and the fixation element for transmitting pressure to the head of the bone screw.

6. The bone anchoring device of claim 5, wherein the pressure element has a cylindrical recess defining two legs and adapted to receive a rod-shaped implant.

7. The bone anchoring device of claim 5, wherein the pressure element comprises a surface having a substantially cylindrical shape adapted to fit with an inner wall of the first bore of the receiving part.

8. The bone anchoring device of claim 1, wherein at least a bottom portion of the first recess of the receiving part has an edge that is chamfered.

9. The bone anchoring device of claim 1, wherein the second recess of the receiving part has a shape that is different from the shape of the first recess of the receiving part.

10. A method of attaching a rod-shaped implant to a bone via a bone anchoring device, the bone anchoring device comprising a bone screw having a threaded section for insertion into a bone, a receiving part having a first end, a second end, a sidewall extending between the first end and the second end, a first bore extending coaxially with a longitudinal axis of the receiving part from the first end, and first and second recesses each extending into the sidewall from the first end, the first and second recesses being positioned and configured for insertion of the rod-shaped implant through the receiving part, and a fixation element configured to fix the rod-shaped implant in the first and second recesses, the rod-shaped implant comprising a rigid first section having a first width, and a stepped portion having a greater thickness than the first width, the method comprising:

attaching the bone anchoring element to a bone;
inserting the rod-shaped implant into the first and second recesses of the receiving part; and
assembling the fixation element to the receiving part to fix the rod-shaped implant, wherein when the receiving part and the fixation element are assembled together, the first recess of the receiving part has a shape of an inverted keyhole, with a bottom section having a second width greater than the first width to accommodate the stepped portion of the rod-shaped implant, and an upper section oriented towards the first end of the receiving part having the first width, and wherein a greatest width of the second recess of the receiving part is less than the second width to accommodate the rigid first section of the rod-shaped implant.

11. A bone anchoring device, comprising:
a rod-shaped implant having a first end, a second end, and a longitudinal axis extending between the first end and the second end, wherein a first width of the rod-shaped implant is a maximum width of the rod-shaped implant measured in a direction perpendicular to the longitudinal axis, and wherein the rod-shaped implant has a portion with a second width that is less than the first width; and
a receiving part for receiving the rod-shaped implant, the receiving part having a first end, a second end, a central axis extending between the first end and the second end, an outer surface, and a recess extending from the first end toward the second end and being configured for insertion of the rod-shaped implant through the receiving part;
wherein the recess of the receiving part forms a shape of an inverted keyhole in the outer surface of the receiving part, wherein a bottom section of the inverted keyhole has a first width measured in a direction perpendicular to the central axis of the receiving part, and an upper section of the inverted keyhole opens towards the first end of the receiving part and has a second width that is smaller than the first width of the receiving part; and
wherein the first width of the recess of the receiving part is at least the first width of the rod-shaped implant, and wherein the second width of the recess of the receiving part is at least the second width of the rod-shaped implant and less than the first width of the rod-shaped implant.

12. The bone anchoring device of claim 11, wherein a portion of the rod-shaped implant having the first width comprises a flexible section.

13. The bone anchoring device of claim 11, wherein when the rod-shaped implant is inserted through the receiving part, a portion of the rod-shaped implant having the first width is insertable past the outer surface and into the recess of the receiving part.

14. The bone anchoring device of claim 13, wherein the portion of the rod-shaped implant having the first width and that is insertable past the outer surface and into the recess of the receiving part is positioned closest to the first end of the receiving part.

* * * * *